US00PP29648P3

(12) United States Plant Patent
Randag

(10) Patent No.: US PP29,648 P3
(45) Date of Patent: Sep. 4, 2018

(54) CALLA LILY PLANT NAMED 'PURPLE SPIRIT'

(50) Latin Name: *Zantedeschia sprengeri*
Varietal Denomination: Purple Spirit

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 47 days.

(21) Appl. No.: 15/530,235

(22) Filed: Dec. 14, 2016

(65) Prior Publication Data

US 2017/0181364 P1 Jun. 22, 2017

Related U.S. Application Data

(60) Provisional application No. 62/386,953, filed on Dec. 17, 2015.

(51) Int. Cl.
*A01H 5/02* (2018.01)

(52) U.S. Cl.
USPC ..... Plt./490

(58) Field of Classification Search
USPC ..... Plt./263.1, 490
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

'Purple Spirit' is a new variety of calla lily having inflorescences with a purple-colored spathe that produces 5-30 inflorescences per tuber. The inflorescence stems are about 20-49 cm in height, and the leaves are green with whitish spots and have a leathery texture.

3 Drawing Sheets

Botanical classification: *Zantedeschia sprengeri.*
Varietal denomination: 'PURPLE SPIRIT'.

BACKGROUND OF THE NEW PLANT

The present invention comprises a new and distinct cultivar of calla lily, botanically known as *Zantedeschia sprengeri* and hereinafter referred to by the cultivar name 'Purple Spirit'.

'Purple Spirit' is a product of a planned breeding program which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z040902-635 (female parent, unpatented) with a *Zantedeschia sprengeri* selection referred to as Z050910-820 (male parent, unpatented). 'Purple Spirit' was selected in 2013 by the inventor in 't Zand, The Netherlands as one flowering plant within the progeny of the stated cross.

The first act of asexual reproduction of 'Purple Spirit' by tissue culture was performed by the inventor in September of 2013 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 9-12 cm pots at 12-14 weeks after planting in 't Zand, The Netherlands under greenhouse conditions, which approximate those generally used in horticultural practice. Color references are made to The 2001

R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Purple Spirit' which, in combination, distinguish this calla lily as a new and distinct cultivar:

1. Large, purple-colored spathes;
2. Compact plant architecture; and
3. High inflorescence production.

Further, when compared to calla lily plant named 'Paco' (U.S. Plant Pat. No. 24,246), the upper and lower surface spathe color of 'Paco' varies between Purple Group RHS N79B and N79D, while the upper and lower surface spathe color of 'Purple Spirit' varies between Red-Purple Group RHS 61A and 71A.

Table 1 provides differences of 'Purple Spirit' to its parents, *Zantedeschia sprengeri* selections Z040902-635 and Z050910-820.

TABLE 1

| 'Purple Spirit' | Differences | |
|---|---|---|
| Z040902-635 | Spathe color | Varies between Red-Purple Group RHS 72B and Purple Group RHS N78C |
| | Plant height | 20-45 cm |
| Z050910-820 | Spathe color | Varies between Red-Purple Group RHS 59B and 60A |
| | Plant height | 35-50 cm |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
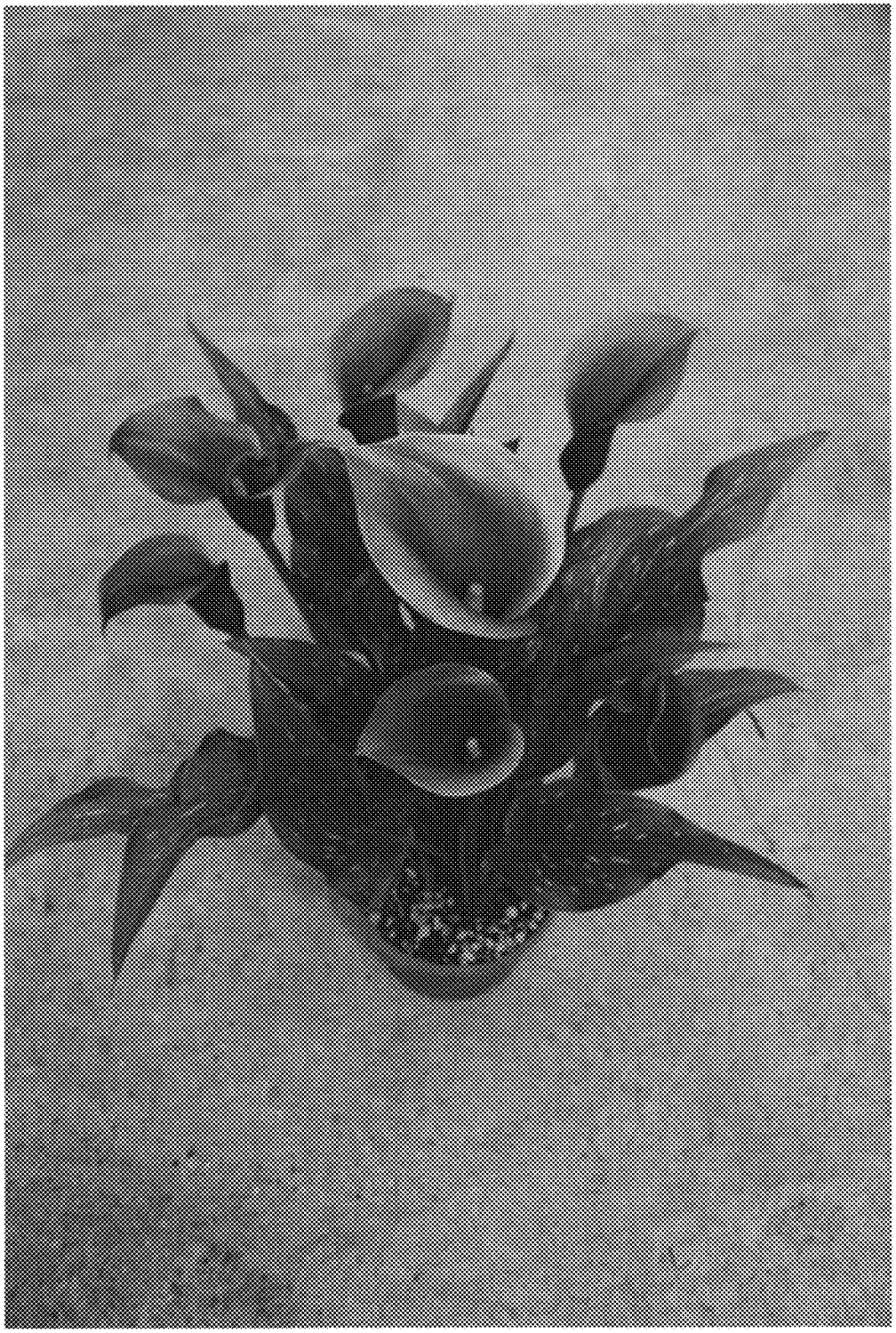
FIG. 1 is a photograph of a top view of a potted plant of the new variety.
Figure 2:
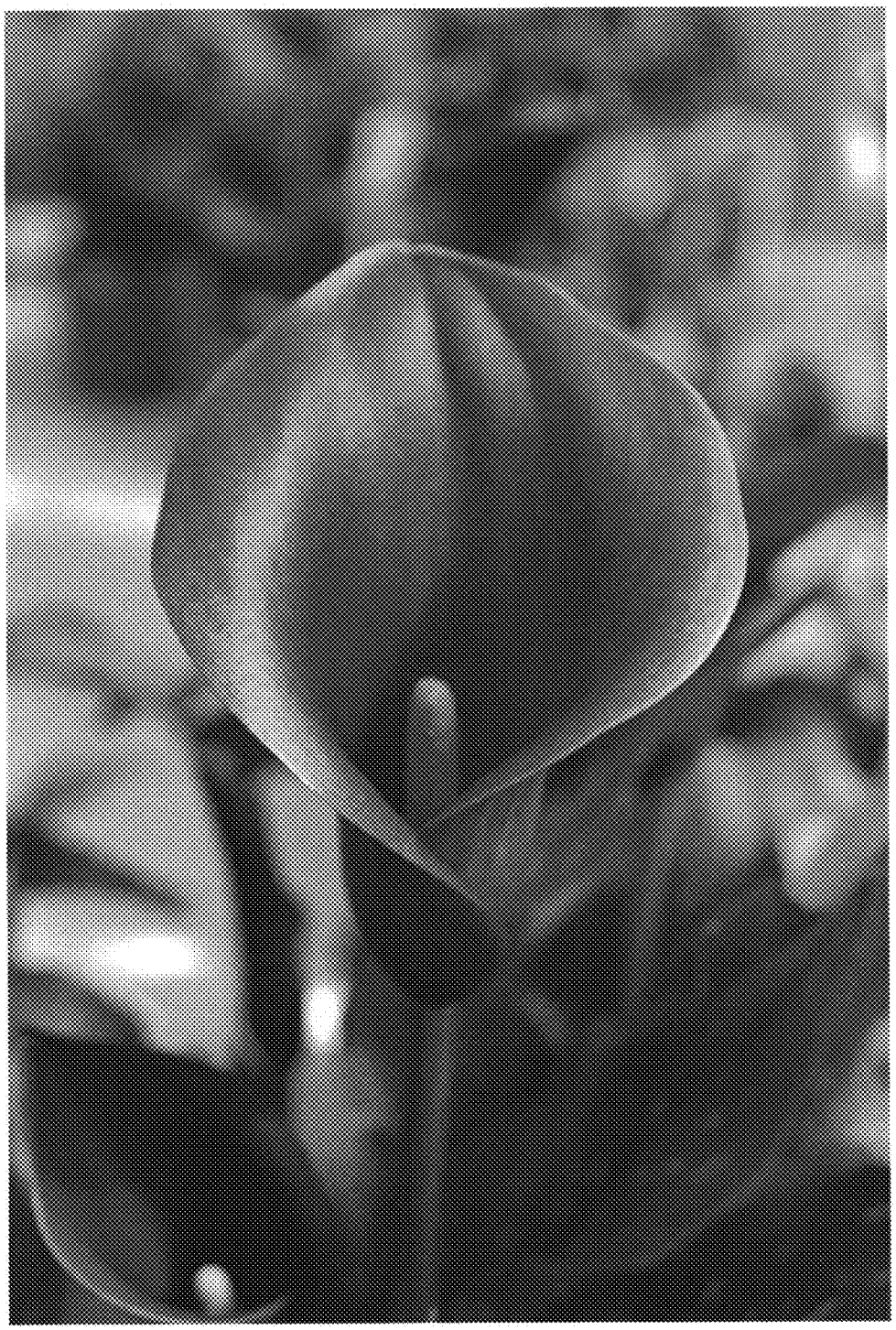
FIG. 2 is a photograph of a close-up view of the new variety.
Figure 3:
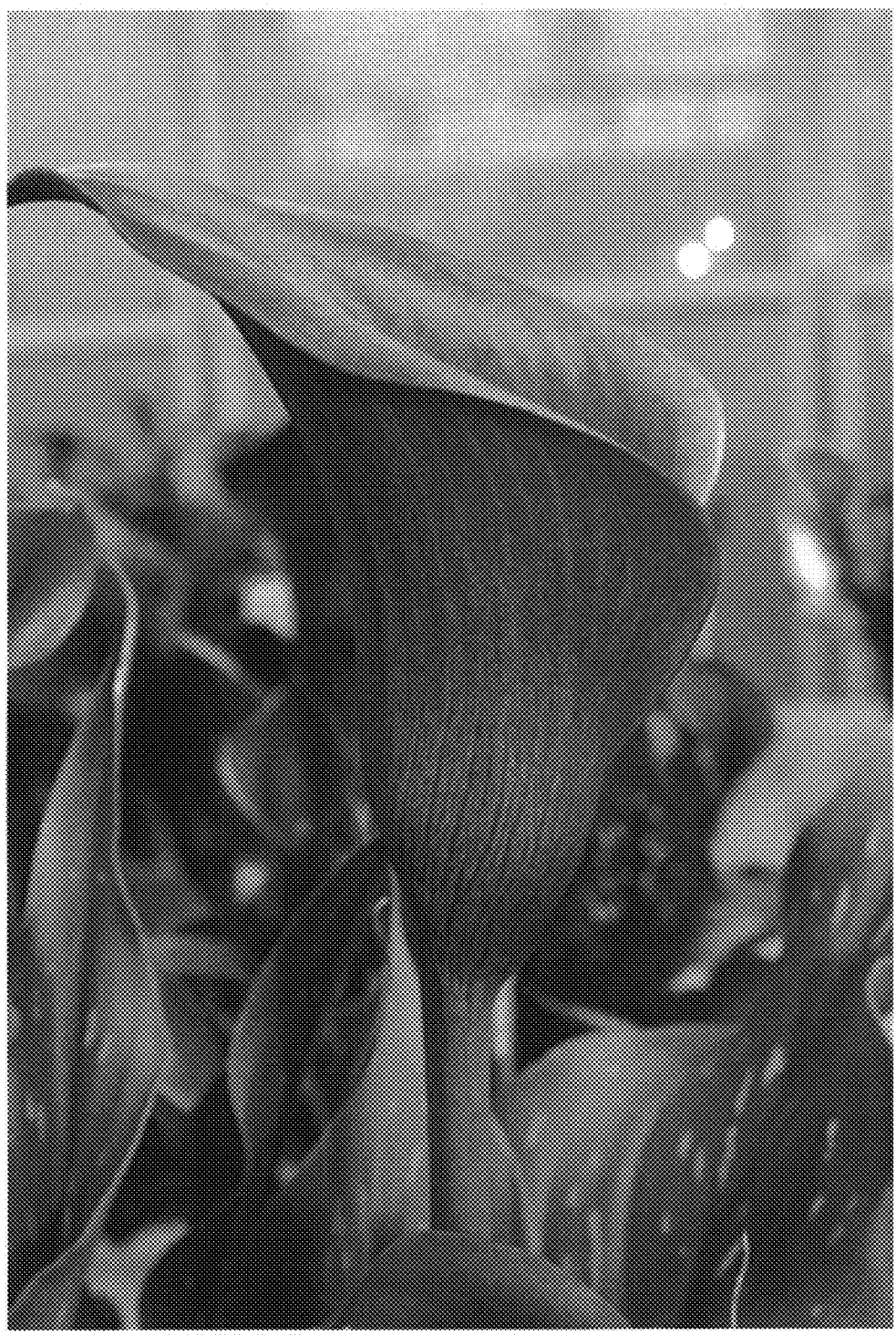
FIG. 3 is a photograph of a side view of the new variety.

Size:
- *Height of the leaf canopy above the soil.*—22-51 cm.
- *Height of top of inflorescence above the soil.*—20-49 cm.
- *Diameter.*—36-49 cm.

Form: Erect.

Number of inflorescences per tuber:
- *Size* 14-16 *cm in diameter.*—5-9 inflorescences.
- *Size* 16-18 *cm in diameter.*—9-16 inflorescences.
- *Size* 18-20 *cm in diameter.*—10-25 inflorescences.
- *Size* 20-22 *cm in diameter.*—15-30 inflorescences.

Branches:
- *Number.*—From 4-10.
- *Color.*—Between Yellow-Green Group RHS 146A and 146C.

Leaves:
- *Size.*—Width: 2.9-8.6 cm. Length: 12-28 cm.
- *Number per plant.*—41-50.
- *Shape.*—Lanceolate.
- *Color.*—Upper surface: Between Green Group RHS 137A to Yellow-Green Group 147A, with transparent White Group RHS 155A and N155A spots. Lower surface: Between Green Group RHS 137A to 137B, with transparent White Group RHS 155A and N155A spots.
- *Apex.*—Apiculate.
- *Base.*—Attenuate.
- *Margin.*—Undulate; having a color between Green Group RHS 137A to 137B.
- *Veins.*—Configuration: Pinnate. Color: Between Yellow-Green Group RHS 146A to 146B.
- *Surface quality.*—Leathery.
- *Petiole.*—Length: 10-23 cm. Average diameter: 10 mm. Color: The base is White Group RHS 155A and the upper part is between Yellow-Green Group RHS 144A to 144C.

Roots:
- *Color.*—White.
- *Branching.*—Similar to other *Zantedeschia* varieties.

The Inflorescence and Seeds

Spathe:
- *Size.*—Length (measured from base opening to tip): 4.9-8.5 cm. Width: 3.2-5.3 cm. Height: 5-11 cm.
- *Color.*—Upper surface: Varies between Red-Purple Group RHS 61A and 71A. Lower surface: Varies between Red-Purple Group RHS 61A and 71A.
- *Vein color.*—Red-Purple Group RHS 61A.
- *Shape.*—Funnel.
- *Apex.*—Attenuate.
- *Base.*—Obtuse.
- *Texture.*—Smooth (upper and lower surfaces).

Spadix:
- *Size.*—Length: 20-40 mm. Diameter: 4-6 mm.
- *Color.*—Varies between Yellow Group RHS 9A and 12A.
- *Position relative to spathe.*—Upright.

Peduncle:
- *Size.*—Length: 15-38 cm. Diameter: 3-8 mm.
- *Color.*—The upper part is between Yellow-Green Group RHS 144A to 144B, and the lower part is Green-White Group RHS 157C.
- *Texture.*—Smooth.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.
- *Anther.*—Shape: Round. Length: Less than 1 mm. Color: Between Yellow Group RHS 9A and 12A.
- *Filament.*—Length: Less than 1 mm. Color: Between White Group RHS 155A and 155B.
- *Pistil.*—Number: 15 to 30. Length beyond perianth: About 1 mm.
- *Stigma.*—Shape: Round. Size: Less than 1 mm.
- *Style.*—Length: Less than 1 mm. Color: Between Red-Purple Group RHS 61A and 71A.
- *Ovaries.*—Texture: Smooth. Length: Between 1 to 10 mm. Width: Between 1 to 10 mm. Color: Top color is between Yellow Group RHS 9A and 12A, bottom color is from White Group RHS 155B to Green-White Group RHS 157C.

Seeds:
- *Length.*—4-7 mm.
- *Width.*—3-6 mm.
- *Color.*—Between Yellow-Green Group RHS 150A and 151A.
- *Amount.*—Between 1-70.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Purple Spirit' as herein described and illustrated.

* * * * *